US012605338B2

(12) United States Patent
    Xiao et al.

(10) Patent No.:    US 12,605,338 B2
(45) Date of Patent:        Apr. 21, 2026

(54) METHOD FOR PREPARING NANO-IMMUNE ACTIVATOR, ARTICLE AND USE THEREOF

(71) Applicant: Southwest University, Chongqing (CN)

(72) Inventors: Bo Xiao, Chongqing (CN); Haiting Xu, Chongqing (CN); Lian Duan, Chongqing (CN)

(73) Assignee: Southwest University, Chongqing (CN)

( * ) Notice: Subject to any disclaimer, the term of this patent is extended or adjusted under 35 U.S.C. 154(b) by 254 days.

(21) Appl. No.: 18/385,915

(22) Filed: Nov. 1, 2023

(65) Prior Publication Data

US 2025/0025424 A1      Jan. 23, 2025

(30) Foreign Application Priority Data

Jul. 21, 2023    (CN) .......................... 202310898401.2

(51) Int. Cl.
_A61K 9/16_                (2006.01)

(52) U.S. Cl.
CPC .......... _A61K 9/1682_ (2013.01); _A61K 9/1658_ (2013.01)

(58) Field of Classification Search
CPC .................................................... A61K 9/1682
See application file for complete search history.

(56) References Cited

FOREIGN PATENT DOCUMENTS

JP          2003002898      *    1/2003

OTHER PUBLICATIONS

Nakeo et al. JP 2003/002898, published: Jan. 8, 2003; English machine translation obtained on Nov. 12, 2025. (Year: 2025).*

Merriam-Webster, "many" definition, 2025. (Year: 2025).*
Zhanying Jiao et al., In Vivo Characterizations of the Immune Properties of Sericin: An Ancient Material with Emerging Value in Biomedical Applications, Macromolecular Bioscience, 2017, p. 1700229, vol. 17, No. 12.
Haifeng Liu et al., Modification of Sericin-free Silk Fibers for Ligament Tissue Engineering Application, Journal of Biomedical Materials Research Part B: Applied Biomaterials, Feb. 22, 2007, pp. 129-138, vol. 82B, No. 1.
Soon-Yong Kwon et al., Silk and collagen scaffolds for tendon reconstruction, Proceedings of the Institution of Mechanical Engineers, Part H: Journal of Engineering in Medicine, Apr. 4, 2014, pp. 388-396, vol. 228, No. 4.
Shuangquan Gou et al., Bioresponsive Self-Reinforcing Sericin/Silk Fibroin Hydrogel for Relieving the Immune-Related Adverse Events in Tumor Immunotherapy, Advanced Functional Materials, Feb. 3, 2023, p. 2213867, vol. 33, No. 15.

* cited by examiner

_Primary Examiner_ — Genevieve S Alley
(74) _Attorney, Agent, or Firm_ — Nitin Kaushik

(57)                ABSTRACT

Provided are a method for preparing a nano-immune activator, and an article and use thereof. The method includes the following steps: acquiring SF and SS; mixing the SF and the SS according to a set mass ratio, and dissolving in double-distilled water to obtain a water phase; injecting the water phase into an acetone solution as an organic phase to obtain a mixed system; subjecting the mixed system to ultrasonic treatment, and stirring until acetone is completely volatilized; conducting centrifugal treatment, and discarding the supernatant; re-adding double-distilled water into a precipitate, carrying out centrifugal treatment, and collecting the supernatant, and repeating the process for many times; subjecting the obtained supernatant to centrifugal treatment; re-adding double-distilled water into the obtained precipitate, and washing for many times to obtain an SF/SS blending complex; dispersing the SF/SS blending complex in a double-distilled water solution containing trehalose; and freeze-drying the mixed solution.

8 Claims, 7 Drawing Sheets a b a b a b a b a b a b

METHOD FOR PREPARING NANO-IMMUNE ACTIVATOR, ARTICLE AND USE THEREOF

CROSS-REFERENCE TO RELATED APPLICATION

The present application claims priority from Chinese Patent Application No. 202310898401.2 filed on Jul. 21, 2023, the contents of which are incorporated herein by reference in their entirety.

TECHNICAL FIELD

The present invention relates to the technical field of development and application of nano immune activators, and in particular to a method for preparing a nano-immune activator, and an article and use thereof.

BACKGROUND

China, as the earliest country of silk reeling and silkworm breeding, has nurtured a long history of silk culture. Silk is a kind of natural protein fiber with a long history. It enjoys the reputation of "queen of fiber" because of its softness, toughness, good luster, light texture, moisture absorption and breathability. Currently, domestic silkworm is the main source of commercial silk. From the chemical composition, silk is a natural protein polymer, which mainly consists of core silk fibroin (SF, 70-75%) and silk sericin (SS, 25-30%) wrapped around the SF. With the progress of science and technology and the cross-integration of multi-disciplines, the application of silk is not limited to the traditional textile field, but has emerged in aspects such as biomedical, flexible electronics and structural materials.

SF was recognized as a biomaterial by the US Food & Drug Administration (FDA) in 1993. Compared with other natural biopolymers, the SF has excellent mechanical properties, good biocompatibility, a low inflammation or immune response, biodegradability and versatility of structural adjustment, and is often used as a biomimic surgical scaffold, wound dressing, micro-nano drug delivery and the like in biomedical related fields. SS, as an adhesive for silk cocoon formation, itself does not have mechanical strength, but has rich biological activities, including natural adhesion to cells, an antioxidant, antithrombin, antibacterial property, inhibiting cell apoptosis, promoting cell differentiation and immunomodulation, etc. However, for decades, the SS has usually been discarded as waste in the silk industry, and is currently removed in a process of processing the SF for medical biomaterials. The SS has become a waste that nobody cares about, because the biological safety of the SS is still controversial. The inflammatory induction, sensitization and immunogenicity of the SS greatly slow down its research in biomedical applications.

Through extensive reference to relevant literature, it has been reported that the SS shows slight inflammatory response and low immunogenicity in vivo through experiments [1], but it is still a safe material suitable for biomedical research. In vivo experiments have showed that pure SS in a form of hydrogel is injected subcutaneously into the back of BALB/c mice, and the SS induced low-level recruitment of infiltrated inflammatory cells with properties similar to alginate and the SF, but much lower than chitosan. In order to further evaluate the immunogenicity of the SS, the ability to induce IgG is evaluated by subcutaneous injection of pure SS, fibrinogen (FIB, a commonly used biomaterial with low immunogenicity), PBS (negative control) and ovalbumin (OVA, positive control). The results have showed that the levels of total IgG and SS-specific IgG in the pure SS group are similar to those in the FIB group and significantly different from those in the OVA group, indicating that the SS has low immunogenicity similar to FIB. It has been concluded that the SS has immunogenicity and will stimulate the immune response of human body. Wang Lin along with her team, through repeated experiments, also has denied the conclusion that the SS has immunogenicity and will stimulate the human body to produce an immune response. After several years of systematic research, Wang Lin's team has extracted a pure SS protein with a complete structure, and has successfully developed SS nerve conduits suitable for peripheral nerve repair, biological scaffolds suitable for central nerve repair, hydrogels for repairing myocardial injury and a variety of multifunctional new drug carriers for the first time in the world. Therefore, the pure SS is a bio-safe biomaterial that can be used in biomedical applications.

Then, the inflammatory response and immunogenicity shown when silkworm raw silk is used as a biomedical material deserve our further consideration [2,3]. Recently, after fully considering the characteristics of the SF and the SS, Gou et al. [4] has designed an SF/SS hydrogel, which system can be used as both a gelling agent and an immunomodulator for anti-tumor immunotherapy research. The results of in vitro transcriptomics analysis have showed that the SF/SS hydrogel system has excellent immunoregulation ability, which can trigger type M2 tumor-associated macrophages to polarize to type M1 and reshape a tumor immunosuppression microenvironment. Furthermore, compared with the control group, the SF/SS hydrogel can further significantly increase the expression of costimulatory factors CD80 and CD86 on the surfaces of dendritic cells in the tumor microenvironment, stimulate them to enhance the presentation of tumor antigens and to stimulate the proliferation and activation behaviors of T cells after activation and maturation, thereby improving the anti-tumor immunotherapy effect.

Currently, the application of the SF/SS blending complex as a nano-immune activator is still blank. Based on this, the present application proposes a method for preparing a nano-immune activator with a suitable and uniform particle size, good biocompatibility and an immune activation performance to fill this blank.

SUMMARY

The technical problem to be solved by the present invention is to provide a method for preparing a nano immune activator, and further provide a nano immune activator article and use of the nano immune activator, in view of the defects in the prior art.

The technical solution adopted by the present invention to solve its technical problem is as follows.

Constructed is a method for preparing a nano-immune activator, which includes the following steps:

step 1: acquiring SF and SS;

step 2: mixing the SF and the SS acquired in the step 1 according to a set mass ratio, and dissolving in double-distilled water to obtain a water phase;

step 3: injecting the water phase obtained in the step 2 into an acetone solution as an organic phase to obtain a mixed system;

step 4: subjecting the mixed system obtained in the step 3 to ultrasonic treatment, and stirring until acetone is completely volatilized;

step 5: subjecting the mixed system obtained in the step 4 to centrifugal treatment, and discarding the supernatant;

step 6: re-adding double-distilled water into a precipitate obtained in the step 5, carrying out centrifugal treatment, and collecting the supernatant, and repeating the process for many times until the mass of the precipitate remains unchanged; step 7: subjecting the supernatant obtained in the step 6 to centrifugal treatment;

step 8: re-adding double-distilled water into the precipitate obtained in the step 7, and washing for many times to obtain an SF/SS blending complex;

step 9: dispersing the SF/SS blending complex obtained in the step 8 in a double-distilled water solution containing trehalose; and step 10: freeze-drying the mixed solution obtained in the step 9.

In the method for preparing a nano-immune activator of the present invention, both the SF and the SS in the step 1 are obtained by extracting and purifying from silk of *Bombyx mori*;

a method adopted for extracting and purifying is:

using $Na_2CO_3$ as a degumming agent to obtain an aqueous solution of the SS, and further subjecting to a dialysis-freeze-drying method to obtain the SS; and oven-drying the remaining SF, dissolving in a ternary solution of $CaCl_2$—$H_2O$—$C_2H_5OH$, and then subjecting to the dialysis-freeze-drying method to obtain an SS protein.

In the method for preparing a nano-immune activator of the present invention, in the step 9, the trehalose is used as a freeze-drying protective agent and accounts for about 5-20% of the total system.

In the method for preparing a nano-immune activator of the present invention, a ratio of a volume of the double-distilled water in the step 2 to acetone in the step 3 is 1:1-1:10.

In the method for preparing a nano-immune activator of the present invention, in the step 10, the freeze-drying is carried out according to the following method: freezing at −20° C. overnight and then placing in a freeze dryer for freeze-drying for 24 h.

In the method for preparing a nano-immune activator of the present invention, in the step 2, the set mass ratio of the SF to the SS is 10:1-1:1.

In the method for preparing a nano-immune activator of the present invention, the ultrasonic treatment in the step 4 is conducted by a method including: performing ultrasonication with a probe ultrasonic instrument at 120 W for 1 min.

In the method for preparing a nano-immune activator of the present invention, the centrifugal treatment in the step 5 is conducted by a method including: centrifuging by a high-speed refrigerated centrifuge at 8,000 RPM/min for 10 min; the centrifugal treatment in the step 6 is conducted by a method comprising: centrifuging by a high-speed refrigerated centrifuge at 6,000 RPM/min for 5 min, and repeating the centrifuging for many times until a mass of a precipitate remains unchanged; and the centrifugal treatment in the step 7 is conducted by a method comprising: centrifuging by a high-speed refrigerated centrifuge at 13,000 RPM/min for 18 min.

Proposed is a nano-immune activator article prepared by adopting the aforementioned method for preparing a nano-immune activator.

Proposed is use of a nano-immune activator, characterized by use of the aforementioned nano-immune activator article in delivery of an oral drug for treating a tumor and microbial infection.

The beneficial effects of the present disclosure are as follows. As verified by experiments, the SF/SS blending complex obtained by application of the method of the present application has a suitable and uniform particle size, good biocompatibility and an immune activation performance. After oral administration, it can activate antigen-presenting cells such as dendritic cells in an intestinal lymphatic tissue, thereby further inducing a mucosal immune response, and improving the therapeutic effect of anti-tumor and microbial infection through lymphatic targeted delivery pathway, which fills the blank of the application of the SF/SS blending complex as an nano-immune activator.

BRIEF DESCRIPTION OF DRAWINGS

In order to explain the embodiments of the present invention or the technical solution in the prior art more clearly, the present invention will be further explained in connection with accompanying drawings and embodiments. The accompanying drawings in the following description show merely some embodiments of the present invention, and those of ordinary skills in the art may still derive other drawings from these accompanying drawings without creative efforts.

DETAILED DESCRIPTION

In order to make the objectives, technical solutions and advantages of the embodiments of the present invention clearer, the following will clearly and completely describe the technical solutions in connection with the embodiments of the present invention, and apparently the described embodiments are a part rather than all of the embodiments of the present invention. All other embodiments obtained by those of ordinary skills in the art based on the embodiments of the present invention without creative efforts are within the claimed scope of the present invention.

Figure 5A:
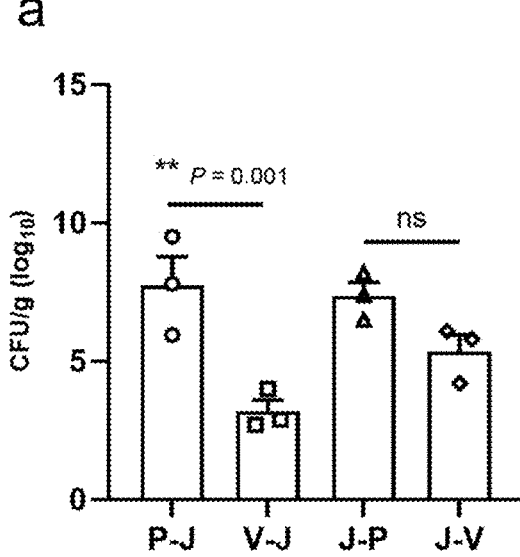
FIG. 5*a* shows the bacterial load in the lungs of mice orally administrated with PBS and SF/SS@Mix/Lip on day 14 after infection with bovine derived *Pasteurella multocida* type A (PmCQ2)
Figure 5B:
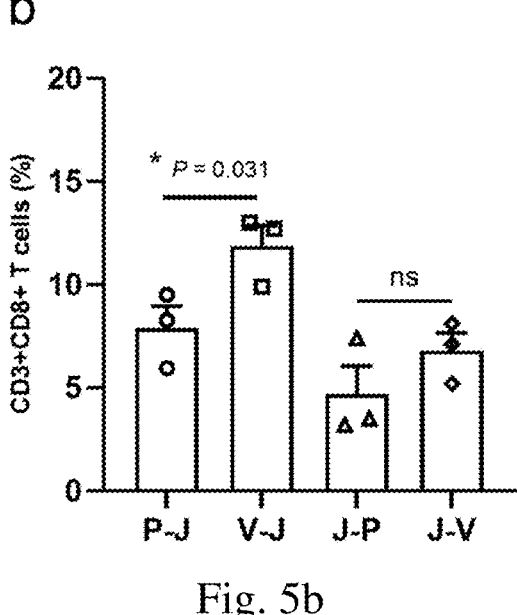
FIG. 5*b* shows the content of $CD8^+$ T cells in a lung tissue suspension after oral administration of PBS and SF/SS@Mix/Lip on day 14 before and after infection with $2.65 \times 10^7$ PmCQ2, as detected by a flow cytometer.
Figure 6A:
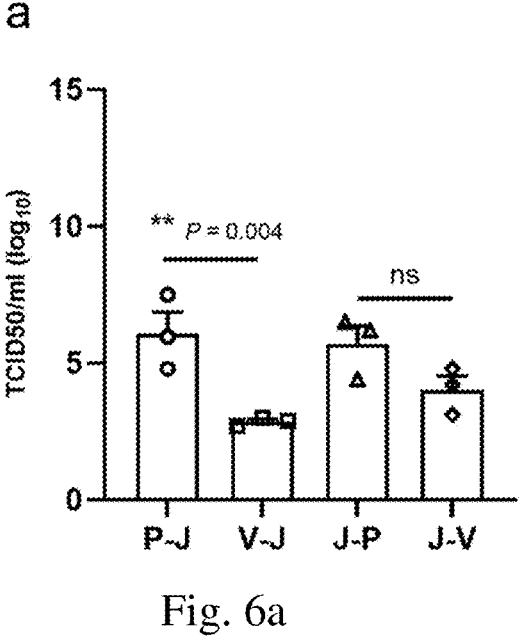
FIG. 6*a* shows the virus titers in the lungs of mice after oral administration of PBS and SF/SS@Mix/Lip on day 14 after infection with bovine derived parainfluenza virus type 3 (BPIV-3)
Figure 6B:
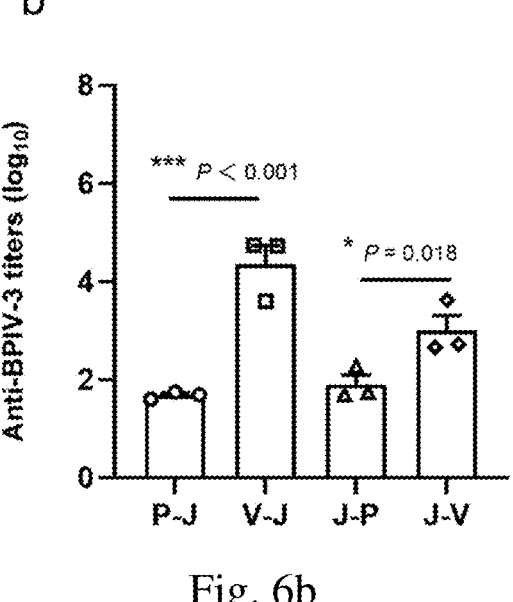
FIG. 6*b* shows a neutralizing antibody titer of the virus in the serum after oral administration of PBS and SF/SS@Mix/Lip on day 14 before and after infection with BPIV-3, as determined by an end-point dilution method.
Figure 7:
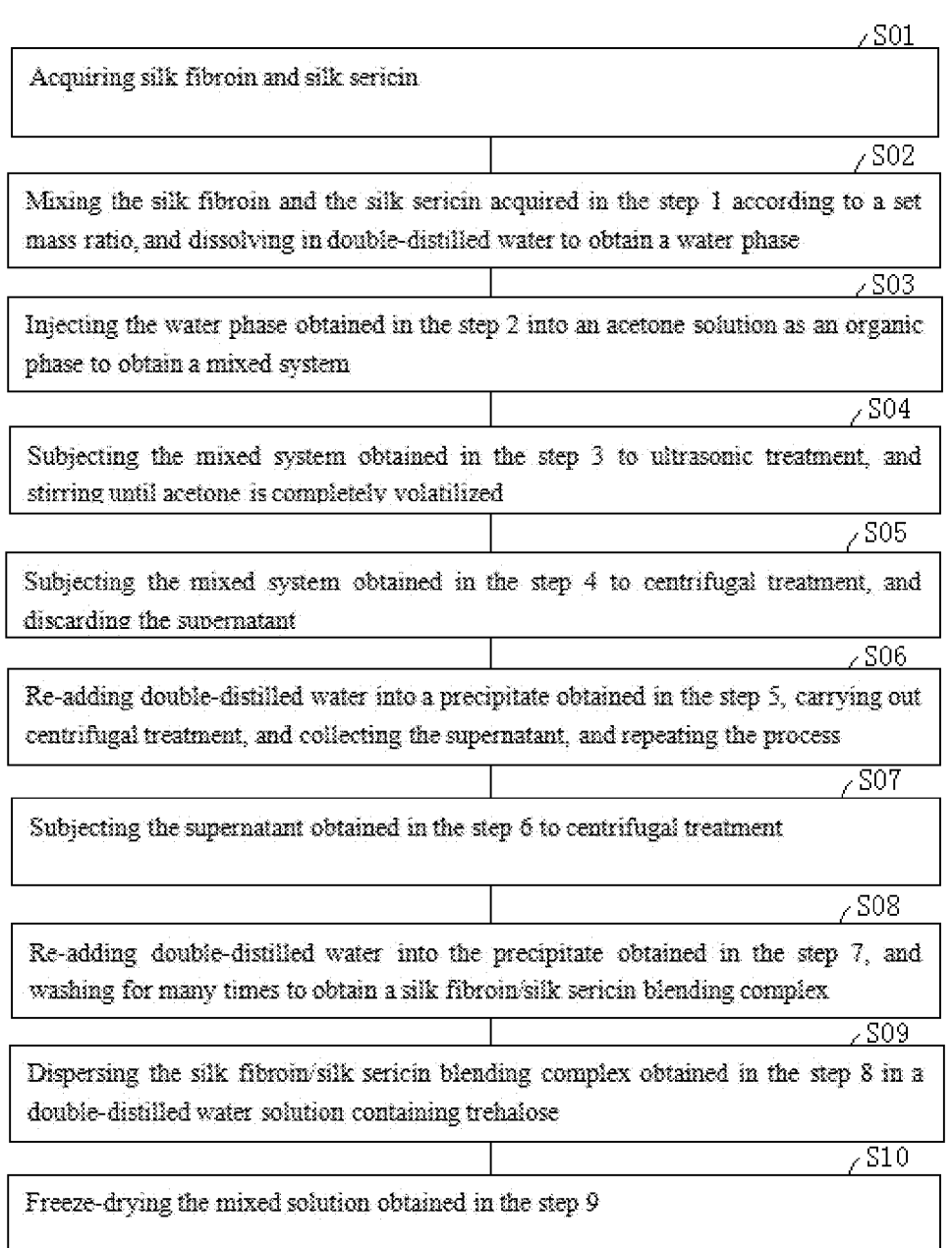
FIG. 7 is a flowchart of a method for preparing a nano-immune activator according to a preferred embodiment of the present invention.

A method for preparing a nano-immune activator according to an preferred embodiment of the present invention, as shown in FIG. 7, meanwhile with reference to FIGS. 1*a*, 1*b*, 2*a*, 2*b*, 3*a*, 3*b*, 4*a*, 4*b*, 5*a*, 5*b*, 6*a*, and 6*b*, includes the following steps:

S01: SF and SS are acquired, wherein both the SF and the SS are obtained by extracting and purifying from silk of *Bombyx mori*; and a method adopted for extracting and purifying is: by using $Na_2CO_3$ as degumming agent, the silk is dissolved in a ternary solution of $CaCl_2$)—$H_2O$—$C_2H_5OH$ and then extracted by a dialysis-freeze-drying method; and of course, other existing purification methods can also be used, which is not limited;

S02: the SF and the SS acquired in the step 1 are mixed according to a set mass ratio, and dissolved in double-distilled water to obtain a water phase, wherein preferably, the mass ratio of the SF to the SS can be selected from 10:1 to 1:1, etc., which can be simply adjusted by those skilled in the art in proportion. Simple adjustment schemes based on this principle all belong to the claimed scope of the present application;

S03: the water phase obtained in the step 2 is injected into an acetone solution as an organic phase to obtain a mixed system, wherein preferably, the volume ratio of double-distilled water in the step 2 to acetone in the step 3 is 1:1-1:10, for example, 8 ml of double-distilled water is adopted, and 40 ml of acetone is adopted, which can be simply adjusted by those skilled in the art in metrology. Simple adjustment schemes based on this principle all belong to the claimed scope of the present application;

S04: the mixed system obtained in the step 3 is subjected to ultrasonic treatment, and stirred until acetone is completely volatilized, wherein as a preferred example, the ultrasonic treatment is conducted by adopting a method including: performing ultrasonication with a probe ultrasonic instrument at 120 W for 1 min, and of course, it can also be adjusted appropriately;

S05: the mixed system obtained in the step 4 is subjected to centrifugal treatment, and the supernatant is discarded, wherein as a preferred example, the centrifugal treatment is conducted by adopting a method including: centrifuging by a high-speed refrigerated centrifuge at 8,000 RPM/min for 10 min; and of course, it can also be adjusted appropriately;

S06: double-distilled water is re-added into a precipitate obtained in the step 5, and subjected to centrifugal treatment, and the supernatant is collected, and the process is repeated for many times until the mass of the precipitate remains unchanged, wherein as a preferred example, the centrifugal treatment is conducted by adopting a method including: centrifuging by a high-speed refrigerated centrifuge at 6,000 RPM/min for 5 min, and of course, it can also be adjusted appropriately;

S07: the supernatant obtained in the step 6 is subjected to centrifugal treatment;

wherein as a preferred example, the centrifugal treatment is conducted by adopting a method including: centrifuging by a high-speed refrigerated centrifuge at 13,000 RPM/min for 18 min, and of course, it can also be adjusted appropriately;

S08: double-distilled water is re-added into the precipitate obtained in the step 7, and the precipitate is washed for many times to obtain an SF/SS blending complex;

S09: the SF/SS blending complex obtained in the step 8 is dispersed in a double-distilled water solution containing trehalose;

wherein preferably, the trehalose is used as a freeze-drying protective agent and accounts for about 5-20% of the total system, and of course, it can also be adjusted appropriately; and S10: the mixed solution obtained in the step 9 is freeze-dried, wherein preferably, the freeze-drying is carried out according to the following method: freezing at −20° C. overnight and then placing in a freeze dryer for freeze-drying for 24 h, and of course, it can also be adjusted appropriately; and the freeze-dried article is stored in a refrigerator at −20° C. for later use.

Proposed is a nano-immune activator article prepared by adopting the aforementioned method for preparing a nano-immune activator.

Proposed is use of a nano-immune activator, characterized by use of the aforementioned nano-immune activator article in delivery of an oral drug for treating a tumor and microbial infection.

As verified by experiments, the SF/SS blending complex obtained by application of the method of the present application has a suitable and uniform particle size, good biocompatibility and an immune activation performance. After oral administration, it can activate antigen-presenting cells such as dendritic cells in an intestinal lymphatic tissue, thereby further inducing a mucosal immune response, and improving the therapeutic effect of anti-tumor and microbial infection through lymphatic targeted delivery pathway, which fills the blank of the application of the SF/SS blending complex as an nano-immune activator.

Experimental verification is as follows:

Experiment 1: Characterization of Physical and Chemical Properties of SF/SS@Mix (SF/SS Blending Complex)

(1) an SF extracted and purified from silk of *Bombyx mori* was provided;

(2) an SS extracted and purified from silk of *Bombyx mori* was provided;

(3) the SF and the SS of the steps (1) and (2) were mixed with a total mass of 100 mg according to mass ratios of 10:1, 5:1 and 2.5:1, and dissolved in double-distilled water to obtain a water phase; and a volume of the double-distilled water was 8 ml;

(4) an acetone solution was used as an organic phase; and a volume of acetone was 40 ml;

(5) the water phase of the step (3) was injected into the organic phase of the step (4);

(6) the mixed system obtained in the step (5) is subjected to ultrasonication with a probe ultrasonic instrument at 120 W for 1 min, and stirred until acetone was completely volatilized;

(7) the mixed system obtained in the step (6) was centrifuged by a high-speed refrigerated centrifuge at 8,000 RPM/min for 10 min, and the supernatant was discarded;

(8) the precipitate obtained in the step (7) was re-added with double-distilled water, and centrifuged by a high-speed refrigerated centrifuge at 6,000 RPM/min for 5 min, and the supernatant was collected, and the process was repeated for 3 times;

(9) the supernatant obtained in the step (8) was centrifuged by a high-speed refrigerated centrifuge at 13,000 RPM/min for 18 min;

(10) the precipitate obtained in the step (9) was re-added with double-distilled water and washed for 3 times;

(11) the SF/SS blending complex obtained in the step (10) was re-dispersed in 1 mL of a double-distilled water solution containing trehalose; and

(12) the mixed solution of the step (11) was frozen at $-20°$ C. overnight, then placed in a freeze dryer for freeze-drying for 24 h, and stored in a refrigerator at $-20°$ C. for later use.

1 mg of SF/SS@Mix nanoparticles were taken and dispersed in 5 ml of double-distilled water. A proper amount of the nano-suspension with the aforementioned concentration was taken to make a sample on a surface of a copper mesh, and the sample was observed for its microscopic morphology and structure by TEM after drying. A proper amount of nano-suspension with the aforementioned concentration was taken, and determined for the particle size and distribution respectively by a DLS particle size analyzer.

FIG. 1$a$ was a TEM diagram of the SF/SS@Mix, and FIG. 1$b$ was a particle size distribution diagram of the SF/SS@Mix. As could be seen from the figures, the TEM images of the SF/SS@Mix all showed suitable and uniform particle sizes, and the DLS test results showed that the SF/SS@Mix had a particle size of 140.28 nm and a PDI of 0.228.

Experiment 2: SF/SS@Mix Stimulated the Maturation of Antigen-Presenting Cells DC2.4

DCs were inoculated in a 12-well plate according to $0.5×10^6$/well, and then co-incubated with Saline, OVA, SS, SF, SF/SS@Mix1 (SF:SS=10:1), SF/SS@Mix2 (SF:SS=5:1), SF/SS@Mix3 (SF:SS=2.5:1), SF/SS@Out1 (SF:SS=10:1), SF/SS@Out2 (SF:SS=5:1), SF/SS@Out3 (SF:SS=2.5:1) respectively at 37° C. under a condition of 5% $CO_2$ for 24 h. SF/SS@Out nanoparticles were prepared by first preparing pure SF nanoparticles by an acetone volatilization method, and then attaching the SS onto the surfaces of the pure SF nanoparticles. The unabsorbed nanoparticles were removed by centrifugation, washed twice with PBS, then resuspended with PBS, and then transferred into sterile 1.5 ml centrifuge tubes respectively. Except for the blank control group, each tube was added with 1 µl of fluorescently labeled antibodies CD80 and CD86 and stained in a refrigerator with protection from light at 4° C. for 20 min. At the same time, simple staining was done, that was, the fluorescently labeled antibodies CD80 and CD86 were added respectively and separately to adjust fluorescence compensation, and subsequently, the cells were centrifuged at 1,000 RPM/min for 3 min, the supernatant was discarded, and then the precipitate was resuspended with 0.2 ml of PBS, loaded onto and analyzed by a flow cytometer.

FIGS. 2$a$ and 2$b$ showed the expression of costimulatory molecules CD80 and CD86 after DCs cells were stimulated with OVA, SF, SS, Mix1, Mix2, Mix3, Out1, Out2 and Out3 at different concentrations and different proportions of SF/SS. It could be seen from the figures that when the total protein concentration reached 50 µg/ml, both Mix2 and Mix3 exhibited significant differences in stimulating the expression of CD80 and CD86 compared with OVA as a model antigen and SF and SS alone, while SF/SS@Out had no effect of stimulating the maturation of DCs after a series of treatments. When the total protein concentration was 200 µg/ml, both the SF/SS@Mix and the SF/SS@Out can stimulate the maturation of DCs, but after treatment with the SF/SS@Mix, the DCs expressed higher levels of CD80 and CD86, which promoted the efficient processing and presentation of antigens.

Experiment 3: Experimental Study of SF/SS@Mix in Treating CT-26 Subcutaneous Tumor in Mice On day 0, $2×10^6$ mouse colon cancer cells (CT-26) were injected subcutaneously into the right side of BALB/c mice. The mice were orally administrated with PBS, a blank oral carrier (Blank@Lip), SF/SS@Mix, SF/SS@Mix/Lip ($C_{[SF+SS]}$=113 µg/mouse) and SF/SS@Mix/Lip ($C_{[SF+SS]}$=200 µg/mouse) on days 3, 6 and 11. The mice treated with PBS were used as a negative control group. The tumor volume was measured by a vernier caliper every other day and calculated by the following equation: tumor volume=length×width×width×½. The mice were euthanized on day 15. The tumor was collected, weighed and digested into a single cell suspension, and analyzed for infiltrated immune cells by flow cytometry.

FIG. 3$a$ showed the tumor weight measured on day 15, and FIG. 3$b$ showed the analysis of $CD3^+CD8^+$ T cells in a tumor tissue by flow cytometry at the end of the experiment in a subcutaneous CT-26 tumor model. As could be seen from the figures, compared with the mice in other groups, the mice in the group orally administrated with the SF/SS@Mix/Lip (calculated per the concentration of [SF/SS], with an administrated dosage of 200 µg/mouse) showed a stronger inhibitory effect on tumor growth. Tumors were collected on day 15. Compared with other groups, the tumor weight of the group orally administrated with the SF/SS@Mix/Lip ($C_{[SF+SS]}$=200 µg/mouse) was also the lowest. The infiltrated immune cells $CD3^+CD8^+$ T cells in the tumor tissue were detected by flow cytometry. Compared with the group orally administrated with PBS, the content of tumor infiltrating $CD3^+CD8^+$ T cells in the CT-26 tumor tissues of the mice immunized with the SF/SS@Mix/Lip ($C_{[SF+SS]}$=200 µg/mouse) increased significantly. Therefore, it showed that oral administration of the SF/SS@Mix/Lip could effectively activate an anti-tumor immune response by increasing the content of $CD8^+$ T cells, so as to significantly inhibit tumor growth.

Experiment 4: Experimental Study on the Protective Immunity of SF/SS@Mix to Mice Infected with H99

C57BL/6 mice were divided into a group first orally administrated with PBS and then infected with H99 (P-J), a group first orally administrated with SF/SS@Mix/Lip and then infected with H99 (V-J), a group first infected with H99 and then orally administrated with PBS (J-P) and a group first infected with H99 and then orally administered with SF/SS@Mix/Lip at a dosage of 100 μl/mouse. The SF/SS@Mix/Lip was administered at a concentration of $C_{[SF/SS]}$=200 g/mouse for three times according to the time interval of days 0, 3 and 8. 5 days after the preventive oral administration for the third time, the mice were anesthetized by intraperitoneal injection of 2% pentobarbital and inoculated with $10^5$ CFU of H99 suspended in 40 μl of PBS. Therapeutic oral administration was started on the third day after infection with bacteria. On day 18, all the mice were euthanized, and the alveolar lavage fluid of the mice was extracted, and detected for the cytokine IFN-γ in the alveolar lavage fluid by an Elisa kit. At the same time, the lung was collected aseptically. The lung was weighed, added with icy and sterile PBS, and grinded with a tissue homogenizer to obtain a tissue suspension of the lung. The diluted tissue suspension was smeared on a solid culture medium, and the colonies were counted after being visible to the naked eye.

Figure 1A:
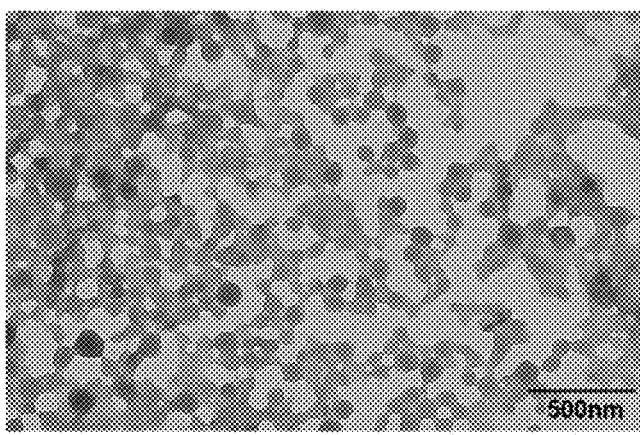
FIG. 1*a* is a TEM diagram of SF/SS@Mix.
Figure 1B:
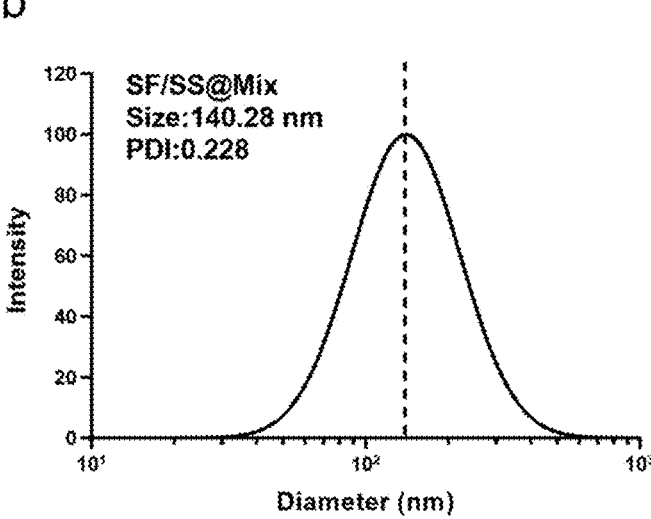
FIG. 1*b* is a particle size distribution diagram of the SF/SS@Mix.
Figure 2A:
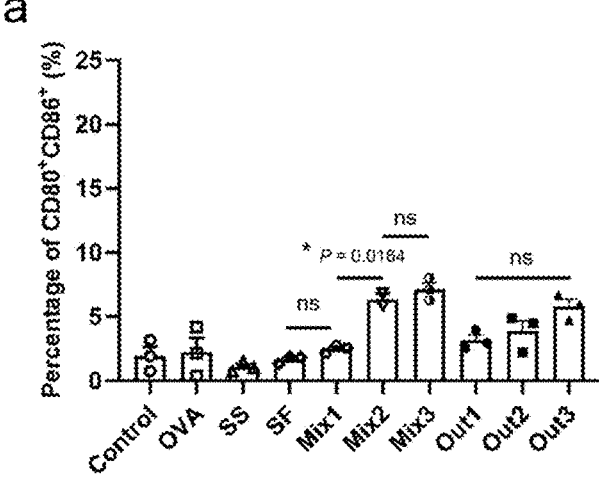
FIG. 2*a* is a schematic diagram of DC2.4 cells treated with OVA, SF, SS, Mix1, Mix2, Mix3, Out1, Out2 and Out3 when $C_{[SF+SS]}$=50 µg/ml.
Figure 2B:
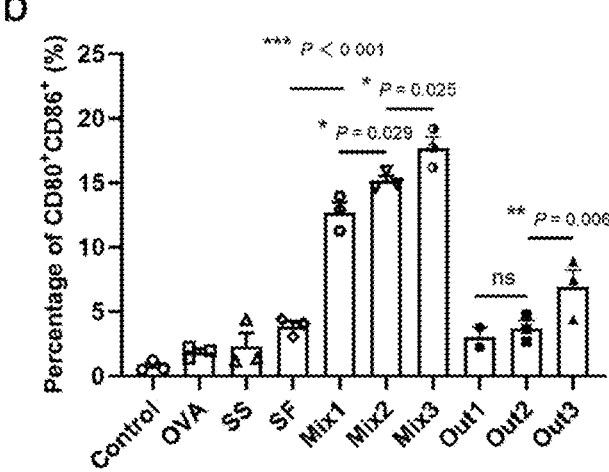
FIG. 2*b* is a schematic diagram of DC2.4 cells treated with OVA, SF, SS, Mix1, Mix2, Mix3, Out1, Out2 and Out3 when $C_{[SF+SS]}$=200 µg/ml.
Figure 3A:
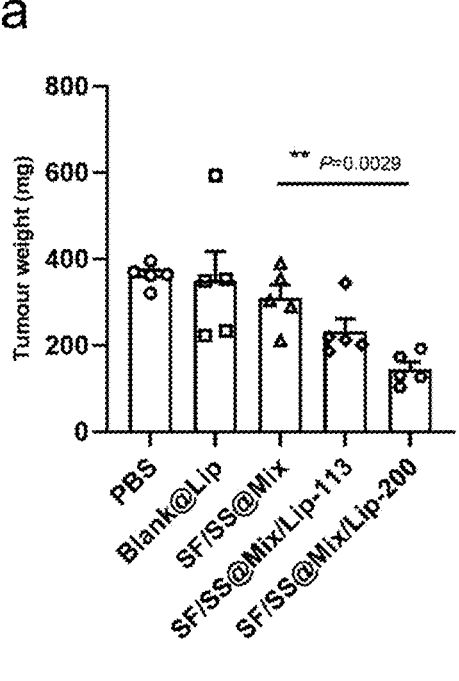
FIG. 3*a* is a schematic diagram of a tumor weight measured on day 15.
Figure 3B:
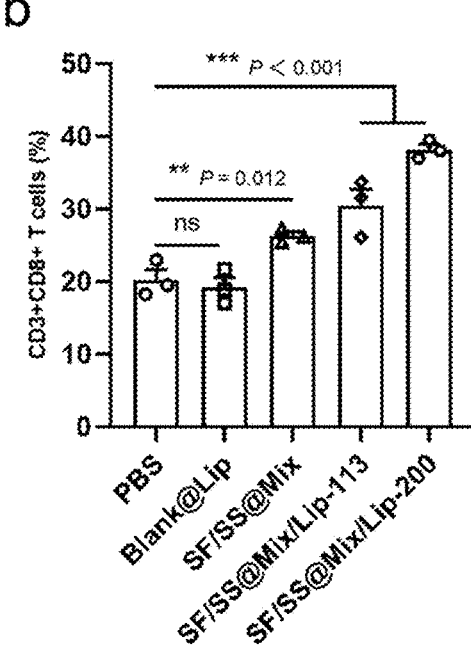
FIG. 3*b* is a schematic diagram of $CD3^+CD8^+$ T cells in a tumor tissue analyzed by flow cytometry at the end of an experiment in a subcutaneous CT-26 tumor model.
Figure 4A:
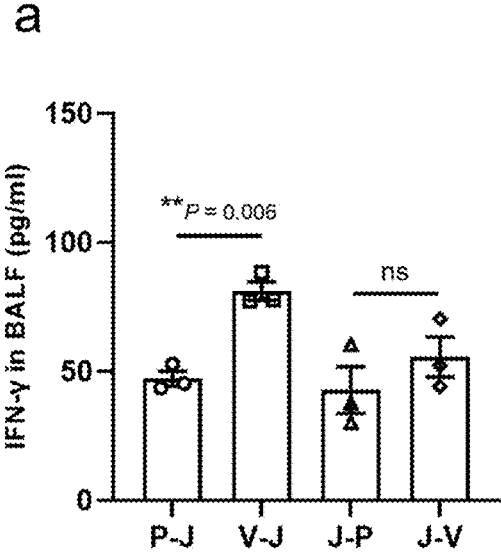
FIG. 4*a* shows the content of IFN-γ in alveolar lavage fluid when PBS (P-J, J-P), preventive (V-J) and therapeutic (J-V) SF/SS@Mix/Lip are orally administrated on day 18 before and after infection with $1 \times 10^5$ *Cryptococcus neoformans* (H99), as detected by an Elisa kit.
Figure 4B:
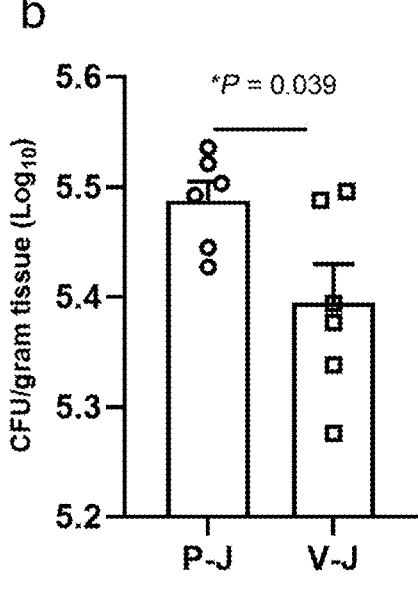
FIG. 4*b* shows the fungal load in the lungs of mice orally administrated with PBS and preventive SF/SS@Mix/Lip on day 18 after infection with H99.

FIG. 4a showed the content of IFN-γ in the alveolar lavage fluid at the end of the experiment when PBS (P-J, J-P), preventive (V-J) and therapeutic (J-V) SF/SS@Mix/Lip were orally administrated before and after infection with 1×10⁵ H99, as detected by an Elisa kit, and FIG. 4b showed the fungal load in the lungs of mice orally administrated with PBS and preventive SF/SS@Mix/Lip on day 18 after infection with H99. As could be seen from the figures, the content of IFN-γ in the alveolar lavage fluid of the mice in the group V-J was significantly higher than that of the oral administration group P-J, while the SF/SS@Mix/Lip had no significant effect on the content of IFN-γ in the alveolar lavage fluid of the oral administration group J-V. It was further found that the CFU counts of H99 as detected in the lungs of the infected animals in the group V-J were significantly lower than those of the mice in the group P-J. Therefore, it was showed that compared with the therapeutic SF/SS@Mix/Lip, oral administration of the preventive SF/SS@Mix/Lip could stimulate a preventive and protective immune response by promoting the production of the type TH1 factor IFN-γ in the alveolar lavage fluid, and thus reduce the load of H99 in the lung.

Experiment 5: Experimental Study on Protective Immunity of SF/SS@Mix to Mice Infected with PmCQ2

KM mice were divided into a group first orally administrated with PBS and then infected with bacterium (P-J), a group first orally administrated with SF/SS@Mix/Lip and then infected with bacterium (V-J), a group first infected with bacterium and then orally administrated with PBS (J-P) and a group first infected with bacterium and then orally administrated with SF/SS@Mix/Lip (J-V) at a dosage of 100 μl/mouse. The SF/SS@Mix/Lip was administered at a concentration of $C_{[SF/SS]}$=200 g/mouse for three times according to the time interval of days 0, 3 and 8.

5 days after preventive oral administration for the third time, the mice were intraperitoneally injected with $2.65×10^7$ CFU of PmCQ2. Therapeutic oral administration was started on the third day after infection with bacteria. On day 14, all the mice were euthanized and their lungs were collected aseptically. The lung was weighed, added with icy and sterile PBS, and grinded with a tissue homogenizer to obtain a tissue suspension of the lung. The tissue suspension was diluted and then smeared on a solid culture medium. The colonies were counted after being visible to the naked eye, and analyzed for the infiltrated immune cells by flow cytometry.

FIG. 5a showed the bacterial load in the lungs of mice orally administrated with PBS and SF/SS@Mix/Lip on day 14 after infection with PmCQ2. FIG. 5b showed the content of CD8⁺ T cells in a lung tissue suspension after oral administration of PBS and SF/SS@Mix/Lip on day 14 before and after infection with $2.65×10^7$ PmCQ2, as detected by a flow cytometer. Compared with the group P-J, the amount of bacterial colonization in the lung tissues of the mice in the group V-J was significantly lower. However, there was no significant difference in bacterial colonization between the group J-P and the group J-V. Similarly, preventive oral administration of SF/SS@Mix/Lip could significantly increase the content of CD8⁺ T cells in the lung tissues of the mice, while therapeutic administration of the SF/SS@Mix/Lip has no significant difference in inhibiting bacterial colonization in the lung. Therefore it indicated that the manner of orally administering SF/SS@Mix/Lip before infection with bacterium could inhibit the proliferation of bacteria in the lungs by increasing the infiltration of CD8⁺ T cells.

Experiment 6: Experimental Study on Protective Immunity of SF/SS@Mix to Mice Infected with BPIV-3

C57BL/6 mice were divided into a group first orally administrated with PBS and then infected with a virus (P-J), a group first orally administrated with SF/SS@Mix/Lip and then infected with a virus (V-J), a group first infected with a virus and then orally administrated with PBS (J-P) and a group first infected with a virus and then orally administrated with SF/SS@Mix/Lip at a dosage of 100 μl/mouse. The SF/SS@Mix/Lip was administered at a concentration of $C_{[SF/SS]}$=200 g/mouse for three times according to the time interval of days 0, 3 and 8. 5 days after the preventive oral administration for the third time, the mice were anesthetized by intraperitoneal injection of 2% pentobarbital and infected by nasal inhalation with $0.5×10^8$ TCID50/BPIV-3 suspended in 50 μl of PBS. Therapeutic oral administration was started on the third day after infection with the virus. On day 14, all of the mice were euthanized, and the eyeball blood of the mice in each group was collected. After separation, the serum was inactivated at 56° C. for 30 min, which was used for detecting the titer of the virus antibody in the serum. meanwhile, their lungs were excised. The collected lung sample was added into a MEM culture solution at an amount of 1 g/ml, grounded into a homogenate, and then freeze-thawed at −80° C. for three times. The diluted homogenate was added into MDBK cells (a 96-well cell culture plate) and continually cultured in an incubator, so as to calculate the results and calculate the lung virus titer.

FIG. 6a showed the virus titers in the lungs of mice after oral administration of PBS and SF/SS@Mix/Lip on day 14 after infection with BPIV-3. FIG. 6b showed a neutralizing antibody titer of the virus in the serum after oral administration of PBS and SF/SS@Mix/Lip on day 14 before and after infection with BPIV-3, as determined by an end-point dilution method. Compared with the group P-J, the amount of viral infection in the lung tissues of the mice in the group V-J was significantly lower. However, oral administration after viral infection basically did not inhibit the amount of virus infection in the lungs. It was found during further detection of the titer of a virus neutralizing antibody in the serum of each group that, preventive oral administration of SF/SS@Mix/Lip significantly improved the titer of the virus neutralizing antibody compared with the group orally administrated with the therapeutic SF/SS@Mix/Lip. Therefore, preventive oral administration of the SF/SS@Mix/Lip could activate the antiviral immune response in vivo by up-regulating the titer of the virus neutralizing antibody, and effectively reduce the virus load in the lungs of the mice infected with BPIV-3.

REFERENCES

[1] Jiao Z, Song Y, Jin Y, et al. In vivo characterizations of the immune properties of sericin: An ancient material with emerging value in biomedical applications[J]. Macromolecular Bioscience, 2017, 17 (12): 1700229.

[2] Liu H, Ge Z, Wang Y, et al. Modification of sericin-free silk fibers for ligament tissue engineering application[J]. Journal of Biomedical Materials Research Part B: Applied Biomaterials, 2007, 82 (1): 129-138.

[3] Kwon S Y, Chung J W, Park H J, et al. Silk and collagen scaffolds for tendon reconstruction[J]. Proceedings of the Institution of Mechanical Engineers, Part H: Journal of Engineering in Medicine, 2014, 228 (4): 388-396.

[4] Gou S, Meng W, Panayi A C, et al. Bioresponsive self-reinforcing sericin/silk fibroin hydrogel for relieving the immune-related adverse events in tumor immunotherapy[J]. Advanced Functional Materials, 2023, 33 (15): 2213867.

Finally, it should be noted that the aforementioned embodiments are only used for illustrating the technical solution of the present invention, but not to limit it. Although the present invention has been described by referring to the preferred embodiments of the present invention, it should be understood by those skilled in the art that various changes can be made in form and detail without departing from the spirit and scope of the present invention as defined in the appended claims.

The invention claimed is:

1. A method for preparing a nano-sized immune activator, comprising the following steps:

step 1: acquiring silk fibroin (SF) and silk sericin (SS);

step 2: mixing the SF and the SS acquired in the step 1 according to a set mass ratio, and dissolving in double-distilled water to obtain a water phase;

step 3: injecting the water phase obtained in the step 2 into an acetone solution as an organic phase to obtain a mixed system;

step 4: subjecting the mixed system obtained in the step 3 to ultrasonic treatment, and stirring until acetone is completely volatilized;

step 5: subjecting the mixed system obtained in the step 4 to centrifugal treatment, and discarding the supernatant;

step 6: resuspending a precipitate obtained in the step 5 in double-distilled water, carrying out centrifugal treatment, and collecting the supernatant, and repeating the process of resuspending the precipitate in double-distilled water, carrying out centrifugal treatment, and collecting the supernatant until the mass of the precipitate remains unchanged;

step 7: subjecting the combined supernatants from all centrifugal treatments obtained in the step 6 to centrifugal treatment;

step 8: adding new double-distilled water into the precipitate obtained in the step 7, and washing to obtain an SF/SS blending complex;

step 9: dispersing the SF/SS blending complex obtained in the step 8 in a double-distilled water solution containing trehalose; and step 10: freeze-drying the mixed solution obtained in the step 9.

2. The method for preparing a nano-sized immune activator according to claim 1, wherein both the SF and the SS in the step 1 are obtained by extracting and purifying from silk of *Bombyx mori;* a method adopted for extracting and purifying is:

using $Na_2CO_3$ as a degumming agent to obtain an aqueous solution of the SS, and further subjecting to a dialysis-freeze-drying method to obtain the SS; and oven-drying the remaining SF, dissolving in a ternary solution of $CaCl_2$—$H_2O$—$C_2H_5OH$, and then subjecting to the dialysis-freeze-drying method to obtain an SF protein.

3. The method for preparing a nano-sized immune activator according to claim 1, wherein in the step 9, the trehalose is used as a freeze-drying protective agent and accounts for about 5-20% of the total system.

4. The method for preparing a nano-sized immune activator according to claim 1, wherein in the step 10, the freeze-drying is carried out according to the following method:

freezing at −20° C. overnight and then placing in a freeze dryer for freeze-drying for 24 h.

5. The method for preparing a nano-sized immune activator according to claim 1, wherein a ratio of a volume of the double-distilled water in the step 2 to acetone in the step 3 is 1:1-1:10.

6. The method for preparing a nano-sized immune activator according to claim 1, wherein in the step 2, the set mass ratio of the SF to the SS is 10:1-1:1.

7. The method for preparing a nano-sized immune activator according to claim 1, wherein the ultrasonic treatment in the step 4 is conducted by a method comprising: performing ultrasonication with a probe ultrasonic instrument at 120 W for 1 min.

8. The method for preparing a nano-sized immune activator according to claim 1, wherein the centrifugal treatment in the step 5 is conducted by a method comprising: centrifuging by a high-speed refrigerated centrifuge at 8,000 RPM/min for 10 min;

the centrifugal treatment in the step 6 is conducted by a method comprising: centrifuging by a high-speed refrigerated centrifuge at 6,000 RPM/min for 5 min, and repeating the centrifuging until a mass of a precipitate remains unchanged; and the centrifugal treatment in the step 7 is conducted by a method comprising: centrifuging by a high-speed refrigerated centrifuge at 13,000 RPM/min for 18 min.

* * * * *